US00PP35639P2

(12) United States Plant Patent
Beers

(10) Patent No.: US PP35,639 P2
(45) Date of Patent: Feb. 6, 2024

(54) ***DIANTHUS* PLANT NAMED 'HILSINCLAIR'**

(50) Latin Name: *Dianthus caryophyllus*
Varietal Denomination: Hilsinclair

(71) Applicant: HilverdaFlorist B.V., De Kwakel (NL)

(72) Inventor: Martin Beers, Hoofddorp (NL)

(73) Assignee: HILVERDAFLORIST B.V., De Kwakel (NL)

( * ) Notice: Subject to any disclaimer, the term of this patent is extended or adjusted under 35 U.S.C. 154(b) by 0 days.

(21) Appl. No.: 18/203,581

(22) Filed: May 30, 2023

(51) Int. Cl.
*A01H 5/02* (2018.01)
*A01H 6/30* (2018.01)

(52) U.S. Cl.
USPC ..... Plt./273

(58) Field of Classification Search
USPC ..... Plt./272, 273
See application file for complete search history.

*Primary Examiner* — Susan McCormick Ewoldt
(74) *Attorney, Agent, or Firm* — C. Anne Whealy

(57) ABSTRACT

A new and distinct cultivar of *Dianthus* plant named 'Hilsinclair', characterized by its compact, upright to outwardly and uniformly mounding plant habit; freely branching habit; relatively broad leaves that are dark green in color; early and freely flowering habit; purple-colored double-type flowers; and good container and garden performance.

2 Drawing Sheets

Figure 1:
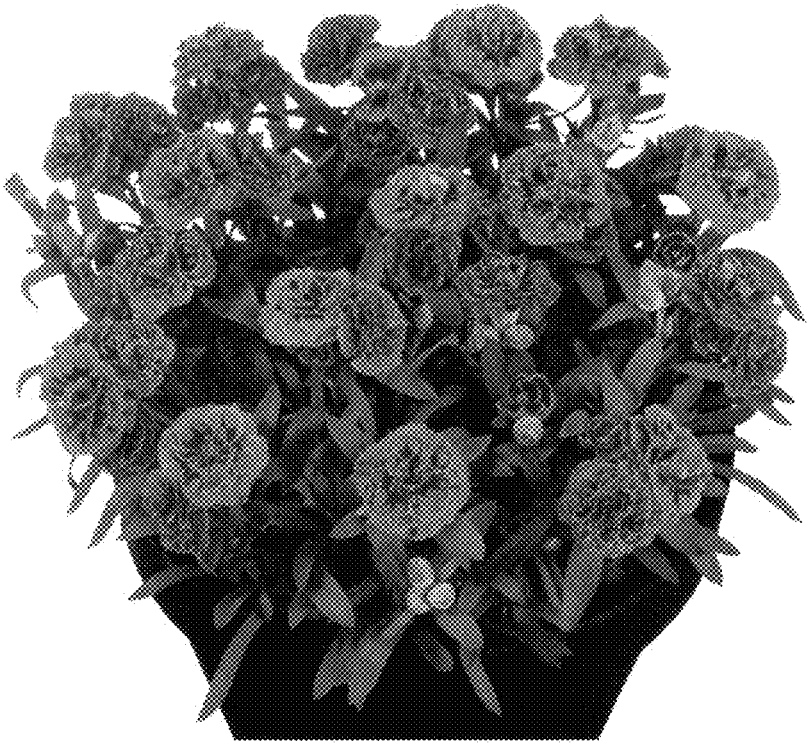

Botanical designation: *Dianthus caryophyllus.*
Cultivar denomination: 'HILSINCLAIR'.

BACKGROUND OF THE INVENTION

The present invention relates to a new and distinct cultivar of *Dianthus* plant, botanically known as *Dianthus caryophyllus* L., grown commercially as a container plant and hereinafter referred to by the name 'Hilsinclair'.

The new *Dianthus* plant is a product of a planned breeding program conducted by the Inventor in De Kwakel, The Netherlands. The objective of the breeding program is to create new container *Dianthus* plants with numerous attractive flowers.

The new *Dianthus* plant originated from a cross-pollination made by the Inventor in De Kwakel, The Netherlands in May, 2014 of a proprietary selection of *Dianthus caryophyllus* L. identified as code number 05065, not patented, as the female, or seed, parent with a proprietary selection of *Dianthus caryophyllus* L. identified as code number 05576, not patented, as the male, or pollen, parent. The new *Dianthus* plant was discovered and selected by the Inventor as a single flowering plant from within the progeny of the stated cross-pollination in a controlled greenhouse environment in De Kwakel, The Netherlands in June, 2015.

Asexual reproduction of the new *Dianthus* plant by terminal cuttings propagated in a controlled greenhouse environment in De Kwakel, The Netherlands since June, 2015 has shown that the unique features of this new *Dianthus* plant are stable and reproduced true to type in successive generations of asexual reproduction.

SUMMARY OF THE INVENTION

Plants of the new *Dianthus* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilsinclair'. These characteristics in combination distinguish 'Hilsinclair' as a new and distinct *Dianthus* plant:

1. Compact, upright to outwardly and uniformly mounding plant habit.
2. Freely branching habit.
3. Relatively broad leaves that are dark green in color.
4. Early and freely flowering habit.
5. Purple-colored double-type flowers.
6. Good container and garden performance.

In side-by-side comparisons, plants of the new *Dianthus* differ primarily from plants of the female parent selection in the following characteristics:

1. Leaves of plants of the new *Dianthus* are broader and are darker green in color than leaves of plants of the female parent selection.
2. Plants of the new *Dianthus* are more freely-flowering than plants of the female parent selection.

In side-by-side comparisons, plants of the new *Dianthus* differ primarily from plants of the male parent selection in the following characteristics:

1. Plants of the new *Dianthus* have slightly lighter green-colored leaves than plants of the male parent selection.
2. Plants of the new *Dianthus* flower earlier than plants of the male parent selection.

Plants of the new *Dianthus* also can be compared to plants of *Dianthus caryophyllus* 'Faganza', disclosed in U.S. Plant Pat. No. 19,757. In side-by-side comparisons, plants of the new *Dianthus* differ primarily from plants of 'Faganza' in the following characteristics:

1. Leaves of plants of the new *Dianthus* are broader than leaves of plants of 'Faganza'.

2. Flowers of plants of the new *Dianthus* are darker purple in color than flowers of plants of 'Faganza'.

BRIEF DESCRIPTION OF THE PHOTOGRAPHS

The accompanying photographs illustrate the overall appearance of the new *Dianthus* plant showing the colors as true as it is reasonably possible to obtain in colored reproductions of this type. Colors in the photographs may differ slightly from the color values cited in the detailed botanical description which accurately describe the colors of the new *Dianthus* plant.

The photograph on the first sheet (FIG. 1) is a side perspective view of a typical flowering plant of 'Hilsinclair' grown in a container.

Figure 2:
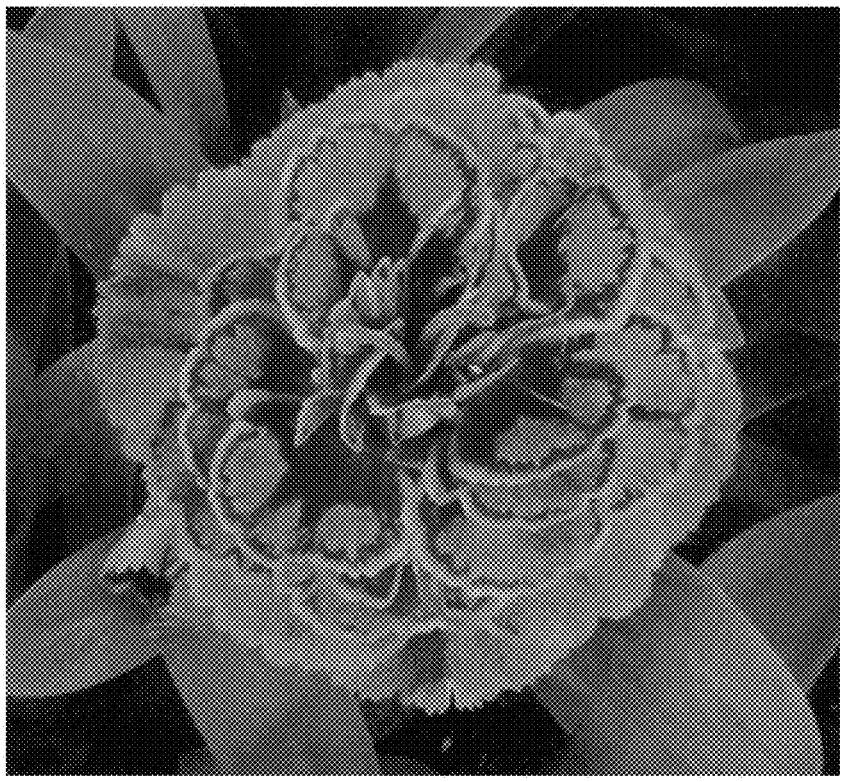

The photograph on the second sheet (FIG. 2) is a close-up view of a typical flower of 'Hilsinclair'.

DETAILED BOTANICAL DESCRIPTION

Plants used in the aforementioned photographs and following observations and measurements were grown during the spring in 10-cm containers in a glass-covered greenhouse in De Kwakel, The Netherlands and under cultural practices typical of commercial container *Dianthus* production. During the production of the plants, day temperatures ranged from 16 C to 20 C and night temperatures ranged from 16 C to 18 C. Plants used for the photographs and description were three months from planting and were pinched one time about one week after planting rooted young plants. In the following description, color references are made to The Royal Horticultural Society Colour Chart, 2015 Edition, except where general terms of ordinary dictionary significance are used.

Botanical classification: *Dianthus caryophyllus* L. 'Hilsinclair'.

Parentage:

*Female, or seed, parent*.—Proprietary selection of *Dianthus caryophyllus* L. identified as code number 05065, not patented.

*Male, or pollen, parent*.—Proprietary selection of *Dianthus caryophyllus* L. identified as code number 05576, not patented.

Propagation:

*Type*.—By terminal vegetative cuttings.

*Time to initiate roots, summer*.—About six days at temperatures ranging from 20 C to 25 C.

*Time to initiate roots, winter*.—About eight days at temperatures about 18 C.

*Time to produce a rooted young plant, summer*.—About three weeks at temperatures ranging from 20 C to 25 C.

*Time to produce a rooted young plant, winter*.—About five weeks at temperatures about 18 C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderate branching; medium density.

Plant description:

*Plant and growth habit*.—Herbaceous perennial, typically grown as a container plant; compact, uniformly mounding, upright to outwardly spreading plant habit; moderately vigorous growth habit; slow to moderate growth rate.

*Plant height, soil level to top of foliar plane*.—About 13.1 cm.

*Plant height, soil level to top of floral plane*.—About 16 cm.

*Plant diameter or spread*.—About 22.8 cm.

*Lateral branches*.—Branching habit: Freely branching habit with about eight main (basal) stems; each main stem with about four to six lateral branches; pinching is not required, however, pinching will enhance lateral branch development. Length: About 11.1 cm. Diameter: About 4 mm. Internode length: About 3.2 cm. Strength: Strong. Aspect: About 15 degrees from vertical. Texture and luster: Smooth, glabrous; glossy overlain with a thin waxy layer which is matte. Color, developing: Close to 145D. Color, developed: Close to 137A; waxy layer, close to 189A.

Leaf description:

*Arrangement*.—Opposite, simple; sessile.

*Length*.—About 10.3 cm.

*Width*.—Relatively broad, about 1.2 cm.

*Shape*.—Narrowly oblanceolate; slightly carinate and slightly curved.

*Apex*.—Acute.

*Base*.—Attenuate; decurrent.

*Margin*.—Entire; not lobed.

*Texture and luster, upper surface*.—Smooth, glabrous; matte.

*Texture and luster, lower surface*.—Smooth, glabrous; slightly glossy overlain with a thin waxy later which is matte.

*Venation pattern*.—Parallel; only midvein is discernible.

*Color*.—Developing leaves, upper surface: Close to 137B. Developing leaves, lower surface: Close to 137C; waxy layer, close to 138B. Fully expanded leaves, upper surface: Close to 147A; venation, close to NN137A. Fully expanded leaves, lower surface: Close to NN137A to NN137B; waxy layer, close to 189A; venation, close to 144A.

Flower description:

*Flower form and flowering habit*.—Rotate double-type flowers arranged singly or in pairs; freely flowering habit with about 34 flower buds and flowers per plant at one time; flowers face mostly upright to slightly outwardly.

*Natural flowering season*.—Flowering is continuous from the spring to late summer in The Netherlands; plants begin flowering about 13 weeks after planting.

*Postproduction longevity*.—Flowers last about ten days on the plant; flowers not persistent.

*Fragrance*.—Faintly fragrant; clove-like, sweet and pleasant.

*Flower buds*.—Length: About 1.8 cm. Diameter: About 1.1 cm. Shape: Rhomboidal. Texture and luster: Smooth, glabrous; slightly glossy. Color: Close to 146B; towards the base, close to 145A; overlain with a thin waxy layer, close to 194B; towards the apex, close to NN74A.

*Flower diameter*.—About 5 cm.

*Flower depth*.—About 3.8 cm.

*Petals*.—Quantity and arrangement: About five petals arranged in a single whorl. Length: About 3.7 cm. Width: About 2 cm. Shape: Spatulate. Apex: Praemorse to narrowly emarginate. Base: Narrowly cuneate. Margin: Distally, irregularly dentate; proximally, entire; moderately undulate. Texture and luster, upper surface: Smooth, glabrous; velvety; matte. Texture and luster, lower surface: Smooth, glabrous; velvety; slightly glossy. Color: When opening, upper surface: Close to NN74A; proximally, "W"-shaped marking, close to 187A and 187B; at the base, close to 145B. When opening, lower surface: Close to 71C; proximally, close to N74C; at the base, close to 145B. Fully developed, upper surface: Close to NN78D; proximally, "W"-shaped marking, slightly more red than N79C; at the base, close to 147D. Fully developed, lower surface: Close to NN78D; proximally, close to 76B; at the base, close to 145B.

*Petaloids*.—Quantity and arrangement: About 30 petaloids arranged in about five whorls. Length: About 3.4 cm; ranging from 2.6 cm to 3.7 cm. Width: About 1.7 cm; ranging from 1.1 cm to 2 cm. Shape: Spatulate. Apex: Praemorse to narrowly emarginate. Base: Narrowly cuneate. Margin: Distally, irregularly dentate; proximally, entire; moderately undulate. Texture and luster, upper surface: Smooth, glabrous; velvety; matte. Texture and luster, lower surface: Smooth, glabrous; velvety; slightly glossy. Color: When opening, upper surface: Close to NN74A; proximally, "W"-shaped marking, close to 187A and 187B; at the base, close to 145B. When opening, lower surface: Close to 71C; proximally, close to N74C; at the base, close to 145B. Fully developed, upper surface: Close to NN78D; proximally, "W"-shaped marking, slightly more red than N79C; at the base, close to 147D. Fully developed, lower surface: Close to NN78D; proximally, close to 76B; at the base, close to 145B.

*Sepals*.—Quantity and arrangement: Five sepals arranged in a single whorl; proximal 73% portion of the sepals are fused into a campanulate-shaped calyx. Calyx length: About 2.2 cm. Calyx diameter: About 1.5 mm. Sepal length: About 2.2 cm. Sepal width, at base of "free" portion: About 6 mm. Shape: Narrowly obovate. Apex: Broadly acute. Margin: Entire. Texture and luster, upper surface: Smooth, glabrous; slightly glossy. Texture and luster, lower surface: Smooth, glabrous; slightly glossy; overlain with a thin waxy layer which is matte. Color: When opening and fully opened, upper surface: Slightly lighter than 147D; apical margins tinged with close to 182B to 182C. When opening and fully opened, lower surface: Close to 138A; towards the base, close to 145B; apical margins, close to 182B; waxy layer, close to 194B.

*Peduncles*.—Length: About 1.1 cm. Diameter: About 1.5 mm to 2 mm. Strength: Moderately strong. Aspect: About 25 degrees from the stem axis. Texture and luster: Smooth, glabrous; moderately glossy overlain with a thin waxy layer which is matte. Color: Close to 143A; waxy layer, close to 188B.

*Pedicels* (*flowers in pairs*).—Length: About 2 mm. Diameter: About 1.5 mm to 2 mm. Strength: Moderately strong. Aspect: About 25 degrees from the peduncle axis. Texture and luster: Smooth, glabrous; moderately glossy overlain with a thin waxy later which is matte. Color: Close to 143A; waxy layer, close to 188B.

*Reproductive organs*.—Stamens: Quantity: Typically ten. Filament length: About 9 mm. Filament color: Close to 157D. Anther size: About 2 mm by 0.5 mm. Anther shape: Irregularly oblong, dorsifixed. Anther color: Close to 16B. Pollen: None observed. Pistils: Quantity: About two per flower. Pistil length: About 1.8 cm. Stigma diameter: About 1 mm. Stigma shape: Pointed, curved. Stigma color: Close to 77A. Style length: About 1.5 cm. Style color: Close to 76D and 77A to 77B. Ovary color: Close to 145B to 145C. Fruits and seeds: To date, fruit and seed development have not been observed on plants of the new *Dianthus*.

Pathogen & pest resistance: To date, plants of the new *Dianthus* have not been observed to be resistant to pathogens and pests common to *Dianthus* plants.

Garden performance: Plants of the new *Dianthus* have been observed to tolerate rain, wind, high temperatures about 35 C and to be suitable for USDA Hardiness Zones 5 to 9.

It is claimed:

1. A new and distinct *Dianthus* plant named 'Hilsinclair' as illustrated and described.

* * * * *